(12) United States Patent
Holman

(10) Patent No.: US 7,314,471 B2
(45) Date of Patent: Jan. 1, 2008

(54) DISPOSABLE SCALPEL WITH RETRACTABLE BLADE

(75) Inventor: Robert Gerard Holman, Sandton (ZA)

(73) Assignee: Trevor John Milton, Johannesburg (ZA)

( * ) Notice: Subject to any disclaimer, the term of this patent is extended or adjusted under 35 U.S.C. 154(b) by 715 days.

(21) Appl. No.: 10/749,691

(22) Filed: Dec. 31, 2003

(65) Prior Publication Data

US 2004/0158269 A1 Aug. 12, 2004

Related U.S. Application Data

(63) Continuation-in-part of application No. 10/657,023, filed on Sep. 5, 2003, now abandoned.

(51) Int. Cl.
*A61B 17/32* (2006.01)
(52) U.S. Cl. .................................................. 606/167
(58) Field of Classification Search ................ 606/167, 606/181, 182, 184, 185; 30/2, 162, 164, 30/286, 335
See application file for complete search history.

(56) References Cited

U.S. PATENT DOCUMENTS

| 5,201,748 | A | 4/1993 | Newman et al. |
|---|---|---|---|
| 5,258,001 | A | 11/1993 | Corman |
| 5,330,493 | A | 7/1994 | Haining |
| 5,403,337 | A | 4/1995 | Platts |
| 5,481,804 | A | 1/1996 | Platts |
| 5,556,409 | A | 9/1996 | Haining |
| 5,571,127 | A | 11/1996 | DeCampli |
| 5,730,751 | A * | 3/1998 | Dillon et al. ................ 606/167 |
| 5,908,432 | A * | 6/1999 | Pan ............................ 606/167 |
| 6,022,364 | A | 2/2000 | Flumene et al. |
| 6,254,621 | B1 | 7/2001 | Shackelford et al. |

* cited by examiner

*Primary Examiner*—Kevin T. Truong
(74) *Attorney, Agent, or Firm*—Meyertons, Hood, Kivlin, Kowert & Goetzel, P.C.; Eric B. Meyertons

(57) ABSTRACT

A scalpel is provided having a handle with a longitudinally extending cavity therein, a blade carrier within the cavity and movable longitudinally relative to the handle between an operative position in which a blade carried thereby is exposed for use at an open end of the cavity and an inoperative position in which a blade carried thereby is retracted within the cavity in the handle, and a manually operable slider associated with the blade carrier and passing through a slot in a wall of the handle at an edge thereof, herein termed the top edge. The handle is moulded as a single piece moulding with an integral bridge defining an endless open end to the cavity through which the blade carrier is introduced into the cavity. The slider is formed as a separate part that snap fits to the blade carrier after its introduction through the open end of the cavity to form a blade carrier and slider assembly. "Click stops" are provided in the operative and inoperative positions by tooth and notch formations on the slider and slot. A final innermost permanently locked position is also preferably provided.

12 Claims, 5 Drawing Sheets

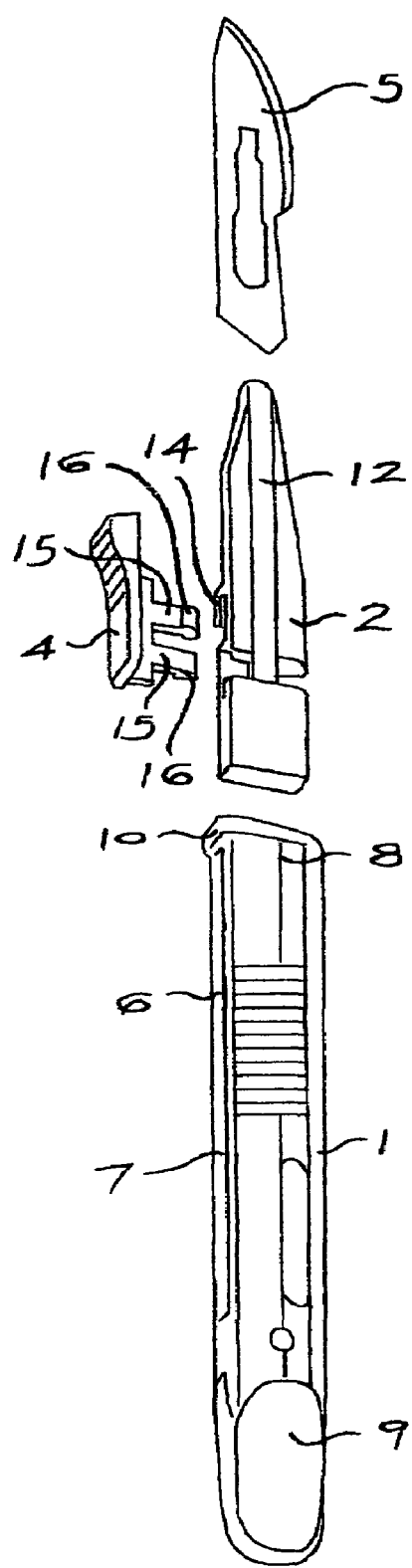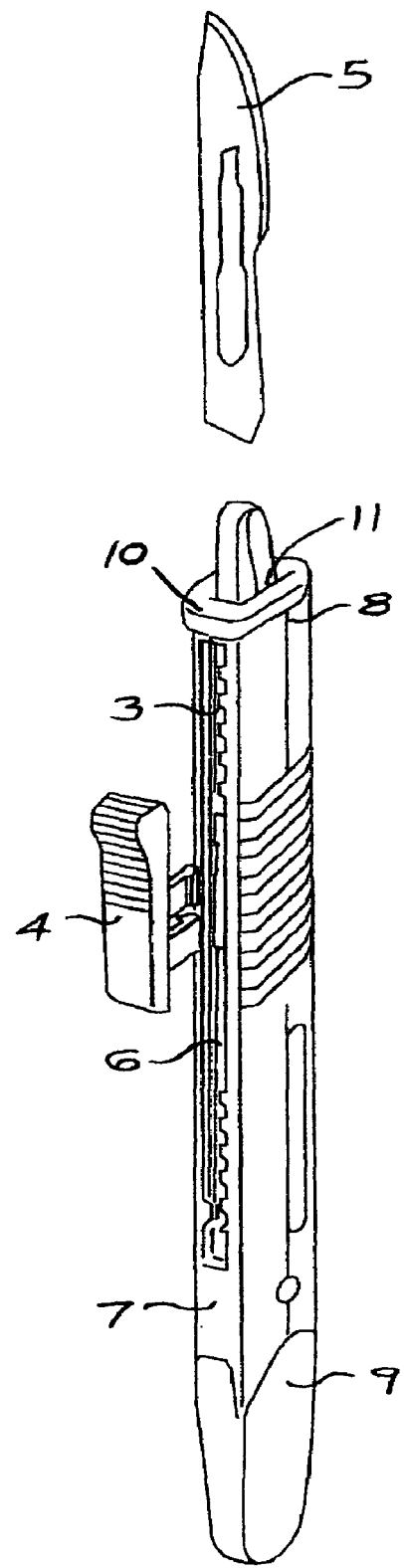

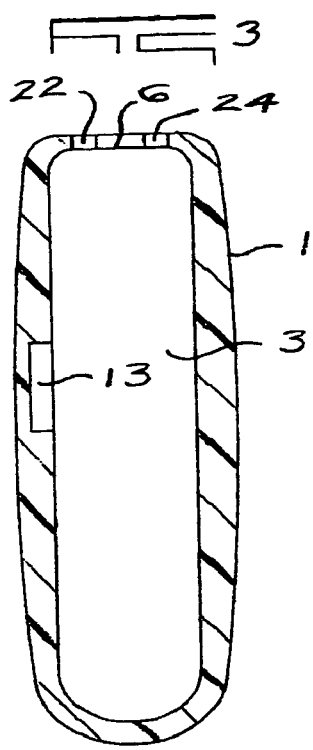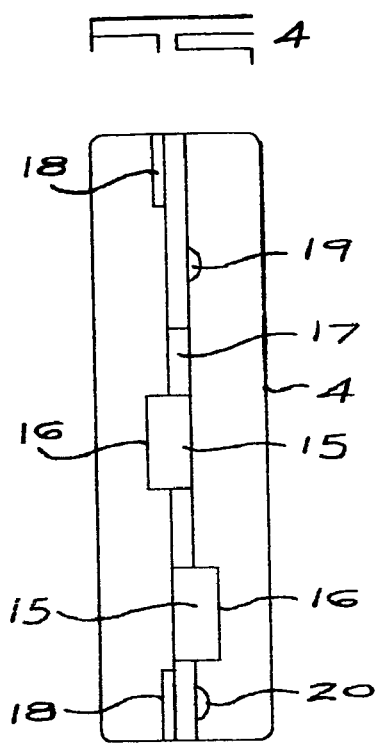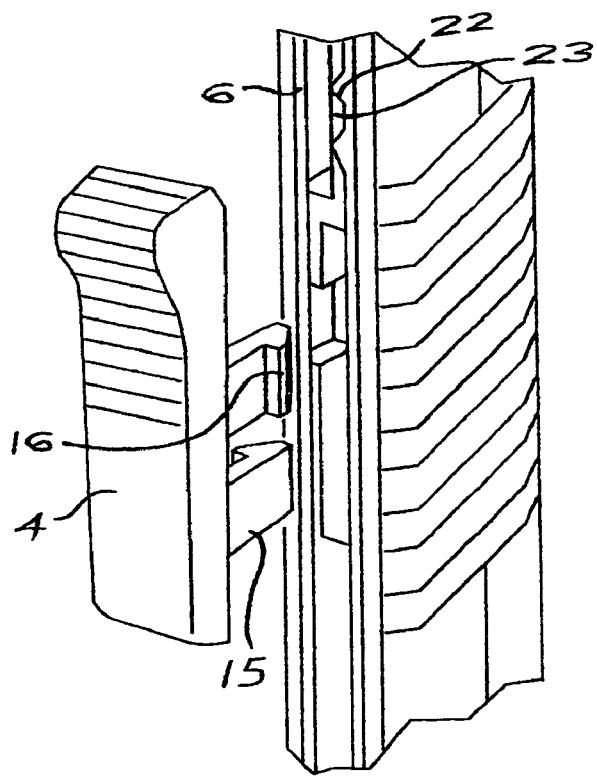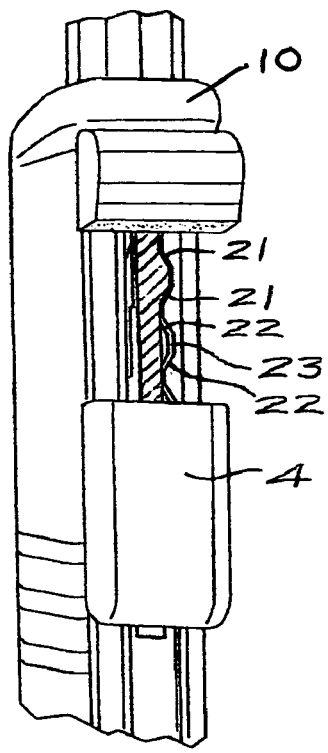

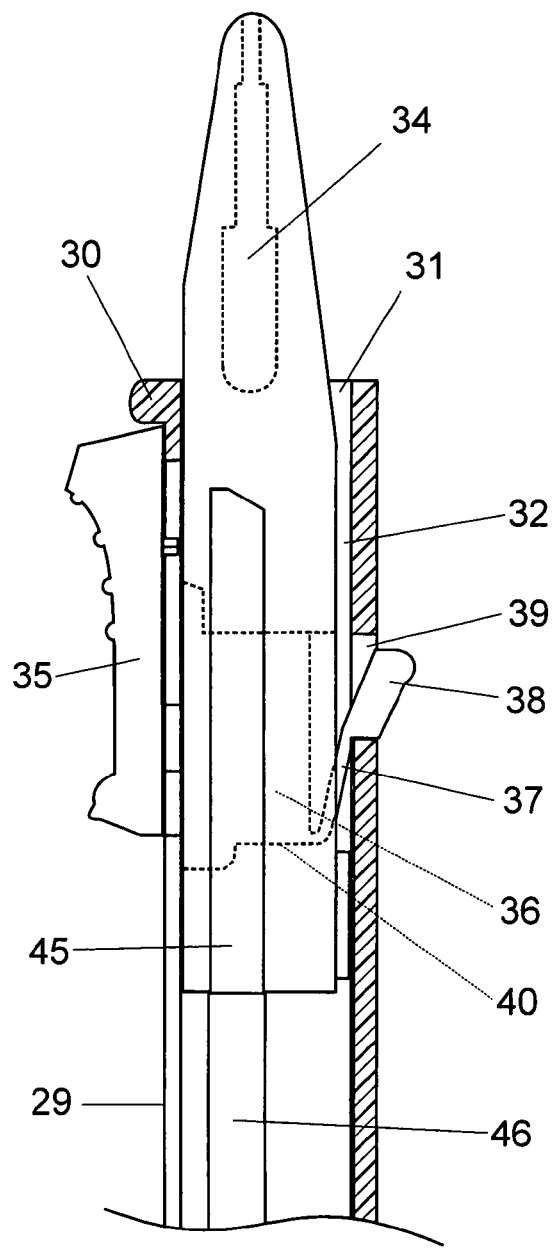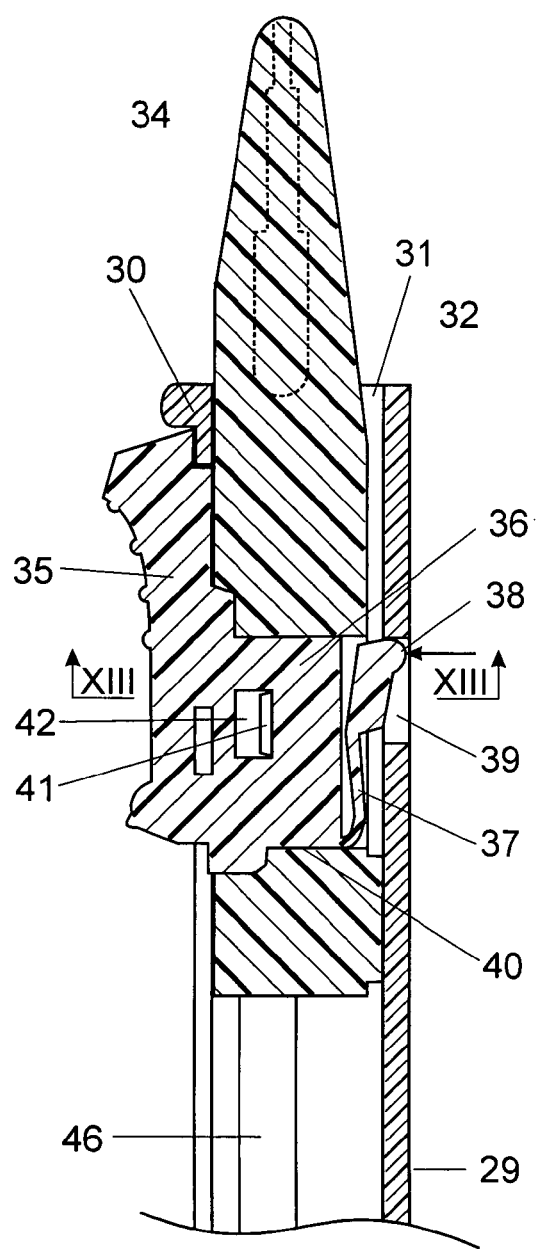

DISPOSABLE SCALPEL WITH RETRACTABLE BLADE

RELATED APPLICATIONS

This application is a continuation-in-part application of U.S. application Ser. No. 10/657,023 filed Sep. 5, 2003 now abandoned that is abandoned in favour of this application.

FIELD OF THE INVENTION

This invention relates to a disposable scalpel having a retractable blade and, more particularly, to a disposable scalpel in which movement of the blade relative to a supporting scalpel handle between an extended operative position and a retracted inoperative position is achieved by moving a blade carrier by way of a thumb operable slider attached, generally by way of a slot through the wall of the handle, to the blade carrier.

BACKGROUND TO THE INVENTION

Disposable scalpels having retractable blades have been proposed and produced in many different forms. The various different forms can, for present purposes, be considered to fall into two different categories; a first being scalpels in which the thumb operable slider projects through a side wall of the scalpel handle, and a second in which the slider projects through a slot in one edge that can be considered to be the top edge of the scalpel handle.

The first type of scalpel that has the slider projecting through a side wall of the handle is considered to suffer from a number of disadvantages, not least of which is that one designed for use by a right-handed person cannot easily be used by a left-handed person and vice versa. U.S. Pat. No. 6,254,621 describes a scalpel that is typical of this type.

The second type of scalpel that has the slider projecting through the top edge of the scalpel handle generally has the disadvantage that the scalpel handle is made in two parts that are subsequently secured together with the blade carrier inside the handle and the associated slider projecting through a slot in the top edge of the composite handle. Typical of this type of construction are the scalpels described in U.S. Pat. Nos. 5,330,493; 5,556,409; and 5,571,127. The two-part construction of the handle is considered by applicant to be undesirable for a variety of reasons not least of which is the fact that the handle could possibly come apart.

There are a number of factors that are independent of the type of construction that are considered to be desirable and that are present to greater or lesser extents in existing scalpels, these being factors that contribute to the scalpel blade being held firmly in its operative position; being held positively in its retracted inoperative position; and also a facility aimed at preventing reuse of a scalpel in an effort to avoid so-called sharps injuries to personnel that may come into contact with used medical equipment.

OBJECT OF THE INVENTION

It is, accordingly, an object of this invention to provide a scalpel with a retractable blade that has one or more improved features over the prior art scalpels of which applicant is aware.

SUMMARY OF THE INVENTION

In accordance with this invention there is provided a scalpel having a handle with a longitudinally extending cavity therein, a blade carrier within the cavity and movable longitudinally relative to the handle between an operative position in which a blade carried thereby is exposed for use at an open end of the cavity and an inoperative position in which a blade carried thereby is retracted within the cavity in the handle, and a manually operable slider associated with the blade carrier and passing through a slot in a wall of the handle at an edge thereof, herein termed the top edge; the scalpel being characterized in that the handle is moulded as a single piece moulding with an integral bridge defining an endless collar encircling the open end of the cavity through which the blade carrier may be introduced into the cavity and in that the slider is formed as a separate part that snap fits to the blade carrier after introduction through the open end of the cavity to form a blade carrier and slider assembly.

Further features of the invention provide for the slider and one or other longitudinally extending edge of the slot to be provided with co-operating tooth and notch formations that cooperate to releasably hold the blade carrier and slider assembly in "click-stop" manner in the operative or inoperative positions, and optionally both; for the blade carrier and slider assembly to have a resiliently biased catch biased towards releasable engagement with a cooperant retaining formation formed integral with the handle, the catch typically being formed integral with either the slider or the blade carrier and being adapted to cooperate with a retaining formation in the form of an aperture through a wall of the handle in the fully extended condition of the blade carrier, the catch typically being releasable by depressing same from outside of the handle; for the blade carrier and slider assembly to have an innermost, terminal locked position defined by co-operating formations on the slider and edges of the slot, such terminal locked position being one in which the blade carrier is located inwards of the normal inoperative position and from which it is substantially impossible to unlock the blade carrier, at least for practical purposes; for a plurality of notches to be associated with both the operative and inoperative positions of the blade carrier and slider assembly so that a series of at least two and optionally three or more "click-stops" are associated with each of the operative and inoperative positions such that a person operating the scalpel will know exactly, by feel, and optionally also hearing, the position of the blade carrier in the handle; and for the tooth and notch formations to be adapted such that an audible "click" is created when a tooth engages a notch.

A further feature of the invention provides for the slider to have either one, or a pair of transverse tongues for cooperating with one or two cooperant transverse sockets formed in the blade carrier with co-operating latch formations serving to substantially permanently lock the slider in association with the blade carrier once installed therein. In the event that there is one tongue it may be generally flat with an aperture therein that its operatively engaged by latch formations on the inside surface of a socket in the blade carrier that receives the tongue. In the event that there are two transverse tongues they are preferably coplanar and spaced apart in the longitudinal direction of the slider.

Preferably, the blade carrier is configured such that it can accept a plurality of different style blades, thereby rendering it more versatile than prior art scalpels.

In order that the invention may be more fully understood two somewhat different embodiments thereof will now be described with reference to the accompanying drawings.

BRIEF DESCRIPTION OF THE DRAWINGS

In the drawings:

FIG. 1 is an exploded perspective view from the side of one embodiment of scalpel according to the invention but offset such that the top edge of the handle is somewhat visible;

FIG. 2 is a similar view, but more from the top, and showing the scalpel partly assembled;

FIG. 3 is a cross-section taken through the handle of the scalpel;

FIG. 4 is an inverted plan view of the slider showing the tooth and slide block formations formed integral therewith;

FIG. 5 is a detail of the slider in its exploded position relative to the blade carrier and as illustrated in FIG. 2;

FIG. 6 is a detail, partly broken away, and showing the cooperation between tooth and notch formations of the slot and slider with the latter in the operative position;

FIG. 10 is a side view of the front end region of a second embodiment of the invention with the handle in section and the blade carrier assembly in full side elevation;

FIG. 11 is a view similar to FIG. 10 but showing the blade carrier and slider in section;

DETAILED DESCRIPTION WITH REFERENCE TO THE DRAWINGS

Figure 7:
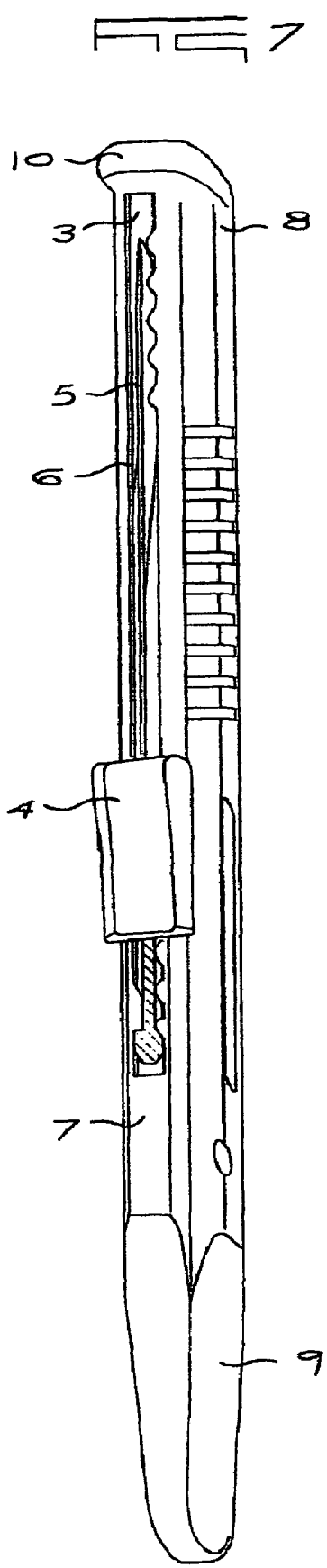
FIG. 7 is a perspective view of the scalpel from one side of the top thereof showing the slider partly broken away in its fully locked position.
Figure 8:
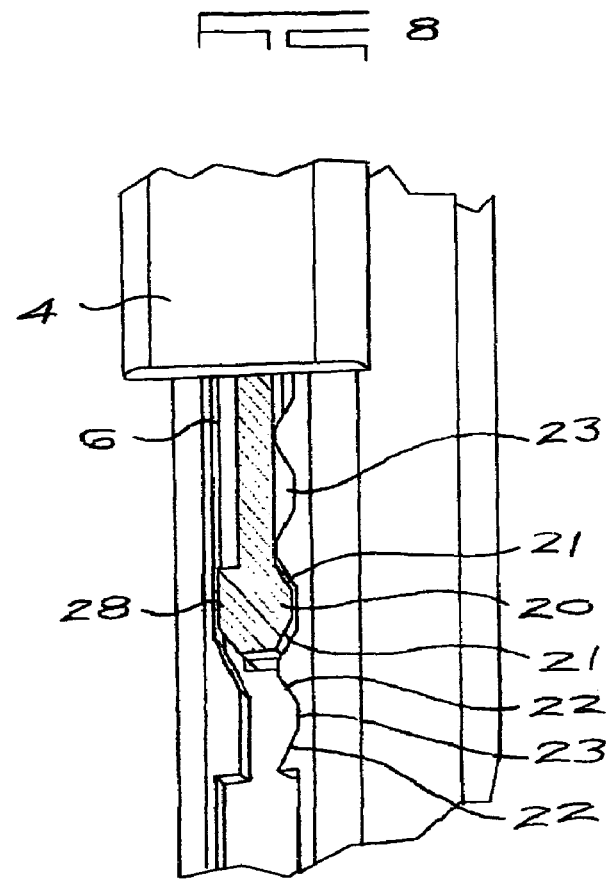
FIG. 8 is a view similar to FIG. 6 showing the cooperation between tooth and notch formations of the slot and slider with the latter in the inoperative position.
Figure 9:
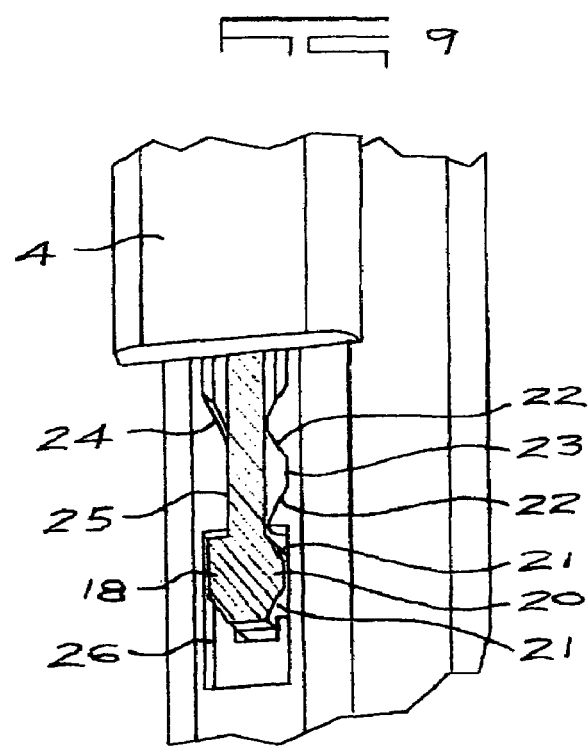
FIG. 9 is a detail similar to FIG. 8 but showing the tooth and notch formations in the final locked position of the slider relative to the scalpel handle (in the position illustrated in FIG. 7)
Figure 13:
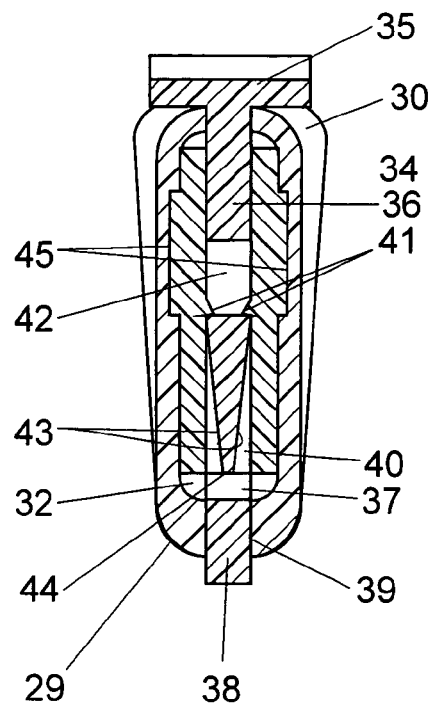

In the embodiment of the invention illustrated in FIGS. 1 to 9 of the drawings, a scalpel comprises a single piece injection moulded plastics handle (1), a blade carrier (2) slidable longitudinally in a longitudinal cavity (3) within the plastics handle, a separately moulded, manually operable slider (4) that combines with the blade carrier to form a blade carrier assembly in the assembled condition, and, for use, a scalpel blade (5) that is fitted to the blade carrier.

The handle has a longitudinally extending slot (6) extending along its operatively top edge (7) from a forward end (8) of the handle towards a rear end (9) thereof and communicating with the cavity inside. An integral bridge (10) at the front end of the top edge forms an endless collar to an open end (11) to the cavity and provides dimensional stability to this end for firmly holding the blade carrier in its operative position.

The blade carrier is elongate and has a longitudinally extending ridge (12) that is received in a cooperating groove (13) (see FIG. 3) on the inner surface of one side wall of the cavity. The blade carrier is configured to slide longitudinally within the cavity and to receive and support a variety of different scalpel blade types. The blade carrier is clearly shaped, in cross-section, to be introduced through the open end (11) to the cavity.

The blade carrier also has a pair of transverse sockets (14) being configured to receive a pair of transverse tongues (15) extending from the slider, the tongues each having a catch formation (16) at its free end that locks onto the blade carrier in irreversible manner when the tongues are introduced into the sockets with the blade carrier in the cavity. Once this has been achieved, the blade carrier is held captive within the cavity and can be slid forwards and rearwards by manually operating the slider, generally by a person holding the scalpel handle and utilizing the thumb to achieve this.

The slider has, on its upper surface, a longitudinally extending ridge (17) that cooperates with the slot to align the slider correctly relative to it. Extending laterally outwards from the ridge at each end thereof is an integral miniature slide block (18) that cooperates with the one edge of the slot and, on the other side of the ridge, are a forward tooth (19) positioned inwards from the nearer end of the ridge and a rearward tooth (20) located opposite the rear slide block (18).

The teeth (19) and (20) are substantially identical and are of trapezoidal or triangular shape to provide inclined faces (21) to cooperate with the inclined edges (22) to notches (23) formed in the associated edge of the slot at both the front and rear ends thereof. In the case of both the front and rear ends of the slot there are provided a series of four juxtaposed notches for cooperation with the forward tooth (19) and rearward tooth (20) respectively when the slider is at the forward or rear ends of the slot.

The arrangement is such that as the slider is moved towards either of the operative or inoperative positions the respective tooth will engage sequentially with the notches of the series of four and will form a "click-stop" in each position. A person operating the slider will be able to feel these sequential "click-stops" and, with appropriate design, also hear them. It will thus be immediately apparent as to the exact location of the blade relative to the handle.

In addition to the above, the rear end of the slot is also provided with a ramp (24) on the side opposite the notches, the ramp communicating with a neck (25) that in turn communicates with a rectangular terminal aperture (26) forming the inner end of the slot. This arrangement is such that when additional force is applied to the slider in a direction towards the rear end of the handle, the slide block (18) and opposite rear tooth (20) are forced together through the neck and into the aperture in an irreversible manner so that the slider is permanently locked in the retracted position. This final position is illustrated clearly in FIG. 9.

It will be understood that, in use, the scalpel may be stored and transported with the blade carrier and associated blade in a retracted position with the slider held in one of the "click-stop" retracted positions. This position may also be used during the conduct of operations in between times when the scalpel is required for use. As and when required, the blade carrier can be moved to present the scalpel blade in its operative position with the blade carrier being arrested in a forward "click-stop" position. The position of the blade relative to the handle can be sensed extremely easily by a person using the scalpel. It is also to be noted that the different "click-stop" positions can be used for the purpose of depth control Once the scalpel has served its purpose and is to be disposed of, the slider is moved to its final locked position so that, to all intents and purposes, it is impossible to use the scalpel again. The scalpel blade is thus held in an extremely safe locked inoperative position for disposal, thereby avoiding the possibility of any so-called sharps injuries.

It will be understood that numerous variations may be made to the embodiment of the invention described above without departing from the scope hereof. Simply by way of example, one alternative arrangement will now be described with reference to FIGS. 10 to 13 of the drawings.

The construction of the scalpel in this case is broadly the same as that described above with the scalpel comprising a handle (29) having a bridge (30) forming an endless collar around an open end (31) of a cavity (32) in the handle; a blade carrier (34); and a separately made slider (35).

Figure 12:
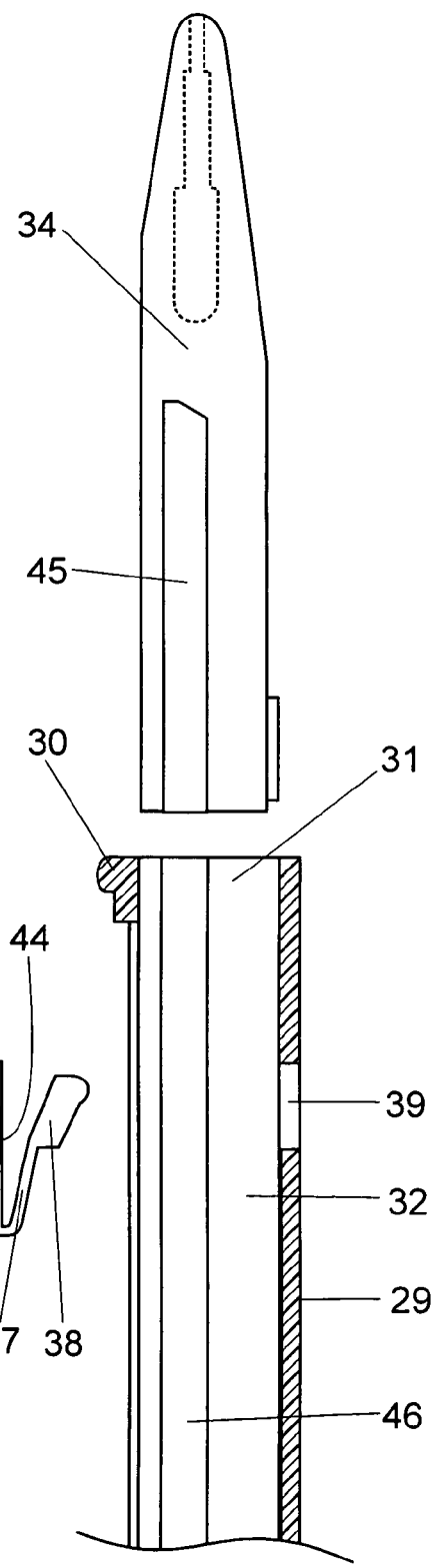
FIG. 12 is an exploded side elevation of the second embodiment of the invention showing only the front end of the handle; and, FIG. 13 is a cross-section taken along line XIII-XIII in FIG. 11.

In this case the slider has a single integral tongue (36) of basically flat shape and having formed integral with its edge opposite the slider an integral resilient arm (37) carrying at its free end a catch (38). The resilient arm extends in the general direction of the length of the handle and is biased to an outer position such as is illustrated in FIG. 12. The catch is arranged to cooperate with a retaining formation in the form of an aperture (39) through the bottom edge of the handle such that the catch registers with, and engages in, the aperture in the fully extended position of the blade carrier, as illustrated in FIG. 10. The arrangement is such that the catch can be depressed into the aperture sufficiently to enable the blade carrier assembly to be selectively slid rearwards to its inoperative position, the disengaged position of the catch, as illustrated in FIG. 11. This arrangement provides an extremely secure locked operative position of the blade carrier for use.

The single tongue (36) is received neatly in a complementary socket (40) formed through the blade carrier and is retained in position by the engagement of two oppositely located ridges (41) formed on the inside surface of the socket to cooperate in latch-like manner with an edge of a rectangular aperture (42) through the tongue. In order to facilitate engagement of the ridges in the aperture, the tongue has a pair of diverging ramp surfaces (43) that commence at an edge (44) of the tongue corresponding to the location of the catch (38). The arrangement is such that the tongue can be forced into the socket to cause the ridges to part as they proceed from the narrow end of the ramp surfaces to the aperture and to snap into position in the aperture when the tongue is fully inserted into the socket. It is thereafter substantially impossible to separate the slider from the blade carrier.

Various other features of the scalpel described with reference to FIGS. 1 to 9 can also be changed. Thus, in this second embodiment of the invention, there is only provided one click stop in each of the operative and inoperative positions of the slider in addition to a final substantially irreversibly locked position for ultimate disposal purposes. Also, in this case, longitudinally extending ridges (45) are provided on the blade carrier in cooperating relationship with grooves (46) on the two opposite surfaces of the inside of the cavity.

It will therefore be understood that numerous other details of the embodiments of the invention described above can be varied without departing from scope hereof which is directed primarily at the two-part construction of the blade carrier assembly.

The invention claimed is:

1. A scalpel having a handle with a longitudinally extending cavity therein, a blade carrier within the cavity and movable longitudinally relative to the handle between an operative position in which the blade carrier extends through an open end of the cavity such that a blade carried thereby is exposed for use and an inoperative position in which the blade carrier is retracted into the cavity such that a blade carried thereby is retracted within the cavity in the handle, and a manually operable slider associated with the blade carrier and passing through a slot in a wall of the handle at an edge thereof, herein termed the top edge; the scalpel handle being molded as a single piece molding with an integral bridge defining an endless collar encircling the open end of the cavity through which the blade carrier may be introduced into the cavity wherein the slider is formed as a separate part that snap fits to the blade carrier after its introduction through the open end of the cavity to form a blade carrier and slider assembly.

2. A scalpel as claimed in claim 1 in which the slider and one or other longitudinally extending edge of the slot are provided with co-operating tooth and notch formations that cooperate to releasably hold the blade carrier and slider assembly in "click-stop" manner in the operative or inoperative positions, and optionally both.

3. A scalpel as claimed in claim 2 in which a plurality of notches are associated with both the operative and inoperative positions of the blade carrier and slider assembly so that a series of at least two, and optionally three or more "click-stops" are associated with each of the operative and inoperative positions.

4. A scalpel as claimed in claim 2 in which the "click-stops" are configured to create an audible sound upon engagement of a tooth with a notch.

5. A scalpel as claimed in claim 1 in which the blade carrier and slider assembly has a resiliently biased catch that is biased towards releasable engagement with a cooperant retaining formation formed integral with the handle in the fully extended condition of the blade earner.

6. A scalpel as claimed in claim 5 in which the catch is formed integral with either the slider or the blade carrier and is adapted to cooperate with a retaining formation in the form of an aperture through a wall of the handle.

7. A scalpel as claimed in claim 6 in which the catch is releasable by depressing same from outside of the handle.

8. A scalpel as claimed in claim 5 in which the catch and a resilient arm carrying same of formed integral with the slider.

9. A scalpel as claimed in claim 1 in which for the blade carrier and slider assembly have an innermost, terminal locked position defined by co-operating formations on the slider and edges of the slot, such terminal locked position being one in which the blade carrier is located inwards of the normal inoperative position and from which it is substantially impossible to unlock the blade carrier, at least for practical purposes.

10. A scalpel as claimed in claim 1 in which the slider has a pair of transverse tongues with oppositely directed catch formations at their inner ends for cooperating with cooperant transverse sockets formed in the blade carrier.

11. A scalpel as claimed in claim 1 in which the slider has a single transverse tongue for cooperating with a cooperant transverse socket formed in the blade carrier with co-operating latch formations serving to substantially permanently lock the slider in association with the blade carrier once installed therein.

12. A scalpel as claimed in claim 1 in which the blade carrier is configured such that it can accept a plurality of different style of blades.

* * * * *